United States Patent
Fattori

(10) Patent No.: US 9,301,821 B2
(45) Date of Patent: Apr. 5, 2016

(54) REFILL HEAD FOR POWERED ORAL CARE IMPLEMENT THAT PRODUCES VIBRATORY AND OSCILLATORY MOTION

(75) Inventor: Joseph E. Fattori, East Sandwich, MA (US)

(73) Assignee: Colgate-Palmolive Company, New York, NY (US)

( * ) Notice: Subject to any disclaimer, the term of this patent is extended or adjusted under 35 U.S.C. 154(b) by 132 days.

(21) Appl. No.: 14/232,253

(22) PCT Filed: Feb. 3, 2012

(86) PCT No.: PCT/US2012/023770
§ 371 (c)(1),
(2), (4) Date: Jan. 11, 2014

(87) PCT Pub. No.: WO2013/009360
PCT Pub. Date: Jan. 17, 2013

(65) Prior Publication Data
US 2014/0165312 A1   Jun. 19, 2014

Related U.S. Application Data

(60) Provisional application No. 61/506,947, filed on Jul. 12, 2011.

(51) Int. Cl.
*A61C 17/34* (2006.01)
*A61C 17/22* (2006.01)

(52) U.S. Cl.
CPC ........... *A61C 17/3472* (2013.01); *A61C 17/222* (2013.01); *A61C 17/3436* (2013.01); *A61C 17/3481* (2013.01)

(58) Field of Classification Search
CPC ...... A46B 13/02; A46B 13/023; A61C 17/22; A61C 17/24; A61C 17/26; A61C 17/32–17/349
USPC ...................... 15/22.1, 22.2, 23, 28
See application file for complete search history.

(56) References Cited

U.S. PATENT DOCUMENTS

| | | |
|---|---|---|
| 2,947,966 A | 8/1960 | Francis |
| 3,369,265 A | 2/1968 | Halberstadt et al. |
| 3,851,984 A | 12/1974 | Crippa |
| 3,927,435 A | 12/1975 | Moret et al. |
| 3,935,869 A | 2/1976 | Reinsch |
| 3,982,808 A | 9/1976 | Marechal |

(Continued)

FOREIGN PATENT DOCUMENTS

| | | |
|---|---|---|
| EP | 0254460 | 1/1988 |
| EP | 0865771 | 9/1998 |

(Continued)

OTHER PUBLICATIONS

Office Action mailed Sep. 30, 2014 in corresponding CO Application No. 14-005019. CO.

(Continued)

*Primary Examiner* — Mark Spisich

(57) ABSTRACT

A refill head, and a powered toothbrush including the same, wherein the refill head comprises a head portion including a movable tuft block that is rotated via operable coupling to a primary drive shaft of the handle. The head portion of the refill head is also receives vibrations from an eccentric that is operated by the primary drive shaft.

14 Claims, 3 Drawing Sheets

(56) References Cited

U.S. PATENT DOCUMENTS

| | | |
|---|---|---|
| 4,348,180 A | 9/1982 | Schuss |
| 4,654,922 A | 4/1987 | Chen |
| 4,683,604 A | 8/1987 | Rueb |
| D297,784 S | 9/1988 | Moret |
| 4,811,445 A | 3/1989 | Lagieski et al. |
| 5,247,716 A | 9/1993 | Bock |
| 5,253,948 A | 10/1993 | Butler |
| 5,361,446 A | 11/1994 | Rufo |
| 5,365,627 A | 11/1994 | Jousson et al. |
| 5,617,602 A | 4/1997 | Okada |
| 5,697,117 A | 12/1997 | Craft |
| 5,768,737 A | 6/1998 | Leutwyler et al. |
| 5,875,510 A | 3/1999 | Lamond et al. |
| 5,974,615 A | 11/1999 | Schwarz-Hartmann et al. |
| 6,138,316 A | 10/2000 | Weihrauch |
| 6,140,723 A | 10/2000 | Matsui et al. |
| 6,145,152 A | 11/2000 | Ward |
| 6,161,244 A | 12/2000 | Jeannet et al. |
| 6,209,164 B1 | 4/2001 | Sato |
| 6,237,183 B1 | 5/2001 | Fischer |
| 6,345,406 B1 | 2/2002 | Dodd |
| 6,360,398 B1 | 3/2002 | Wiegner et al. |
| 6,364,681 B1 | 4/2002 | Watanabe |
| 6,438,784 B1 | 8/2002 | Yu |
| 6,487,748 B1 | 12/2002 | Dardar et al. |
| 6,507,971 B2 | 1/2003 | Sham |
| 6,536,066 B2 | 3/2003 | Dickie |
| 6,546,585 B1 | 4/2003 | Blaustein et al. |
| 6,550,095 B2 | 4/2003 | Hawkins et al. |
| 6,685,375 B1 | 2/2004 | Crocker |
| 6,709,185 B2 | 3/2004 | Lefevre |
| 6,775,875 B2 | 8/2004 | Ornelas et al. |
| 6,889,401 B2 | 5/2005 | Fattori et al. |
| 6,968,590 B2 | 11/2005 | Ponzini |
| 7,111,350 B2 | 9/2006 | Blackman et al. |
| 7,137,166 B1 | 11/2006 | Kraemer |
| 7,222,381 B2 | 5/2007 | Kraemer |
| 7,310,844 B1 | 12/2007 | Rehkemper |
| 7,386,904 B2 | 6/2008 | Fattori |
| 7,386,913 B2 | 6/2008 | Jackson |
| 7,409,741 B2 | 8/2008 | Dworzan |
| 7,424,764 B2 | 9/2008 | Trenz et al. |
| 7,845,039 B2 | 12/2010 | Chan et al. |
| 7,849,548 B2 | 12/2010 | Bock |
| 7,886,393 B2 | 2/2011 | Sorrentino |
| 7,917,984 B2 | 4/2011 | Blaustein |
| 2003/0099508 A1 | 5/2003 | Lefevre |
| 2003/0182743 A1 | 10/2003 | Gatzemeyer et al. |
| 2004/0016073 A1 | 1/2004 | Knutson |
| 2005/0273951 A1 | 12/2005 | Karl |
| 2006/0037158 A1 | 2/2006 | Foley et al. |
| 2007/0256262 A1 | 11/2007 | Moss |
| 2008/0066251 A1* | 3/2008 | Chenvainu ............... A46B 7/06 15/167.1 |
| 2010/0043156 A1 | 2/2010 | Kressner |
| 2010/0101032 A1 | 4/2010 | Kressner |
| 2010/0269275 A1 | 10/2010 | Shimoyama et al. |
| 2010/0325823 A1 | 12/2010 | Kressner |
| 2011/0083288 A1 | 4/2011 | Kressner |

FOREIGN PATENT DOCUMENTS

| | | |
|---|---|---|
| FR | 2 476 994 | 9/1981 |
| JP | 3-261407 | * 11/1991 |
| WO | WO96/22038 | 7/1996 |
| WO | WO2004/019728 | 3/2004 |
| WO | WO2004/024021 | 3/2004 |
| WO | WO2004/049861 | 6/2004 |
| WO | WO2004/049968 | 6/2004 |
| WO | WO2006/071260 | 7/2006 |
| WO | WO2007/072192 | 6/2007 |
| WO | WO2008/014403 | 1/2008 |
| WO | WO2008/074412 | 6/2008 |
| WO | 2009/138638 | * 11/2009 |
| WO | WO2011/044284 | 4/2011 |

OTHER PUBLICATIONS

International Search Report and the Written Opinion issued in International Application PCT/US2012/023766 mailed Jun. 21, 2012.
International Search Report and the Written Opinion issued in International Application PCT/US2012/023768 mailed Jun. 21, 2012.
International Search Report and the Written Opinion issued in International Application PCT/US2012/023770 mailed Jun. 21, 2012.
Written Opinion of the International Preliminary Examining Authority issued in International Application PCT/US2012/023770 mailed Jul. 2, 2013.
International Search Report and the Written Opinion issued in International Application PCT/US2012/023776 mailed Jun. 21, 2012.
Written Opinion of the International Preliminary Examining Authority issued in International Application PCT/US2012/023776 mailed Aug. 20, 2013.
International Search Report and the Written Opinion issued in International Application PCT/US2012/023779 mailed Jun. 21, 2012.
International Search Report and the Written Opinion issued in International Application PCT/US2012/023780 mailed Jun. 29, 2012.
Written Opinion of the International Preliminary Examining Authority issued in International Application PCT/US2012/023780 mailed Jul. 2, 2013.

* cited by examiner

REFILL HEAD FOR POWERED ORAL CARE IMPLEMENT THAT PRODUCES VIBRATORY AND OSCILLATORY MOTION

CROSS-REFERENCE TO RELATED APPLICATIONS

This application is a U.S. national stage application under 35 U.S.C. §371 of PCT Application No. PCT/US2012/023770, filed Feb. 3, 2012, which claims the benefit of U.S. Provisional Patent Application No. 61/506,947, filed on Jul. 12, 2011, the contents of which are hereby incorporated by reference in their entireties.

FIELD OF THE INVENTION

The present invention relates generally to oral care implements, and specifically to powered oral care implements of the type that utilize refill heads that produce motion.

BACKGROUND OF THE INVENTION

Powered toothbrushes having replaceable heads, commonly referred to as refill heads, are known in the art. Such powered toothbrushes typically include a handle and a refill head that is detachably coupled to the handle. The replaceability of the heads in such powered toothbrushes is desirous because the handle, which includes the expensive motion-inducing circuitry and components, is expensive to manufacture and has a much longer life expectancy than do the cleaning elements, such as bristles, that are on the head. Consumers would not be willing to pay a premium to purchase such powered toothbrushes if they had to be discarded when the bristles or other cleaning elements wore out. Thus, it is now standard in the industry to provide refill heads that can be attached and detached from the handle so that worn out refill heads can be replaced as needed while keeping the same handle.

Known toothbrushes that utilize refill heads produce only one type of movement, either vibratory or rotary. Thus, a need exists for a powered oral care implement, and refill head for the same, that can produce both vibratory and oscillatory motion.

BRIEF SUMMARY OF THE INVENTION

The present invention is directed to a refill head, and a powered toothbrush including the same, wherein the refill head comprises a head portion including a movable tuft block that is rotated via operable coupling to a primary drive shaft of the handle. The head portion of the refill head also receives vibrations from an eccentric that is operated by the primary drive shaft.

In one embodiment, the invention can be a powered toothbrush comprising: a handle comprising: a gripping portion; and a stem extending from the gripping portion, the stem extending along an axis; and a power source, an electric motor and a primary drive shaft operably coupled together, the primary drive shaft comprising a distal portion protruding from a distal end of the stem and an eccentric disposed within stem; a refill head detachably coupled to the handle, the refill head comprising: a head portion comprising at least one movable tuft block comprising a plurality of tooth cleaning elements; a tubular sleeve coupled to the head portion, the tubular sleeve having a cavity in which the stem is disposed; and the distal portion of the primary drive shaft operably coupled to the movable tuft block; and wherein rotation of the primary drive shaft by the motor results in: (1) the eccentric of the drive generating vibrations within the stem that are transmitted to the head portion; and (2) rotational movement of the movable tuft block.

In another embodiment, the invention can be a refill head for a powered toothbrush handle comprising: a head portion comprising at least one movable tuft block comprising a plurality of tooth cleaning elements; a tubular sleeve coupled to the head portion, the tubular sleeve having a cavity for receiving a stem of the powered toothbrush handle; a drive shaft adapter having an axial cavity for slidably receiving a distal portion of a primary drive shaft of the powered toothbrush handle, the drive shaft coupler located in a distal portion of the cavity; a secondary drive shaft having a first end operably coupled to the movable tuft block and a second end operably coupled to the drive shaft adapter; and the tubular sleeve comprising a vibration transmission portion configured to be in intimate surface contact with an outer surface of the stem of the powered toothbrush handle, the vibration transmission portion located at a middle portion of the cavity.

In yet another embodiment, the invention can be a refill head for a powered toothbrush handle comprising: a head portion comprising at least rotatable tuft block comprising a plurality of tooth cleaning elements; a tubular sleeve coupled to the head portion, the tubular sleeve having a cavity for receiving a stem of the powered toothbrush handle; a drive shaft adapter operably coupling a distal portion of a primary drive shaft of the powered toothbrush handle to the rotatable tuft block; and the tubular sleeve comprising a vibration transmission portion configured to be in intimate surface contact with an outer surface of the stem of the powered toothbrush handle.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
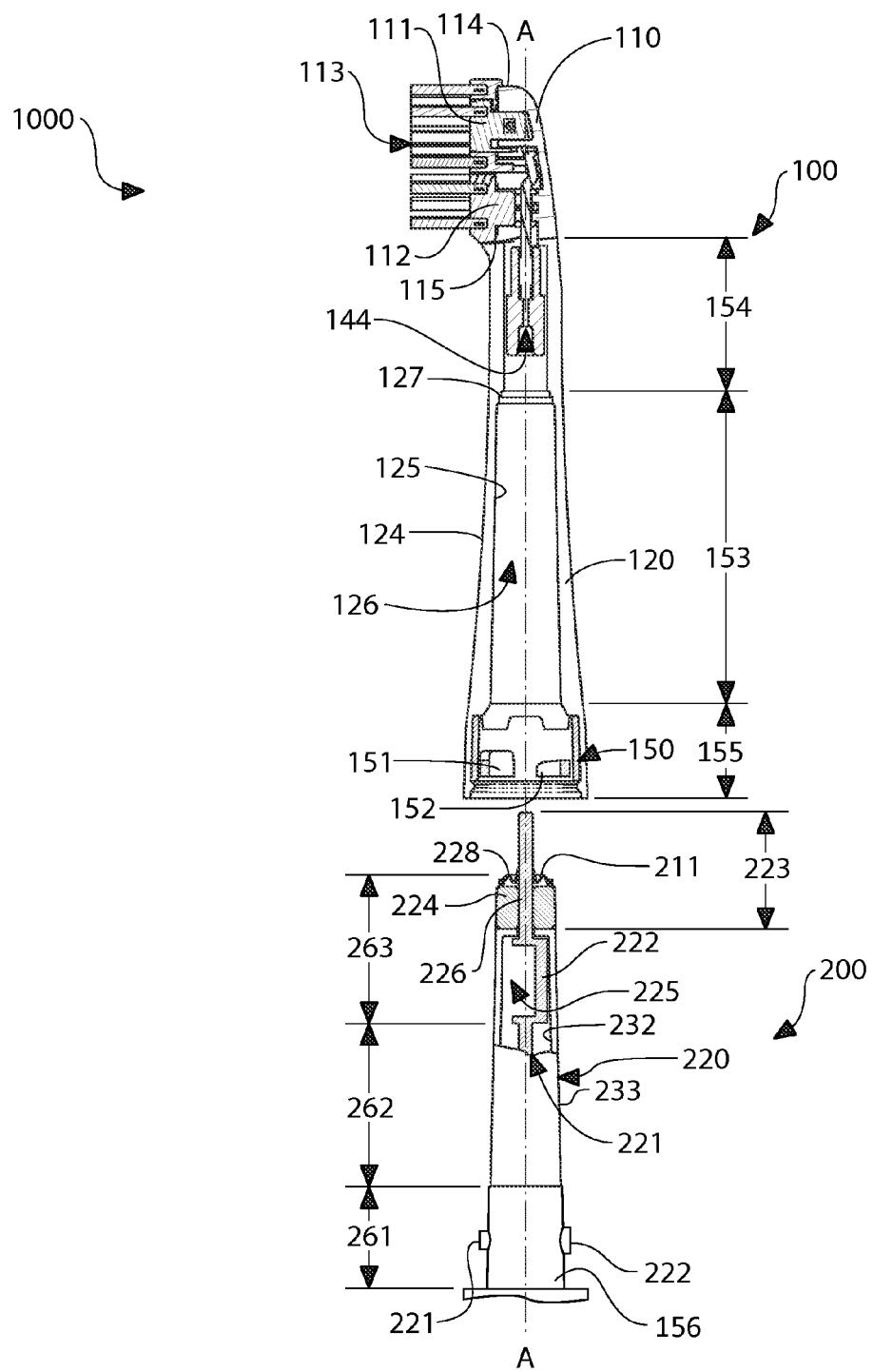
FIG. 1 is a front view of a refill head and a powered toothbrush handle in alignment for detachable coupling according to one embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above,"

"below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
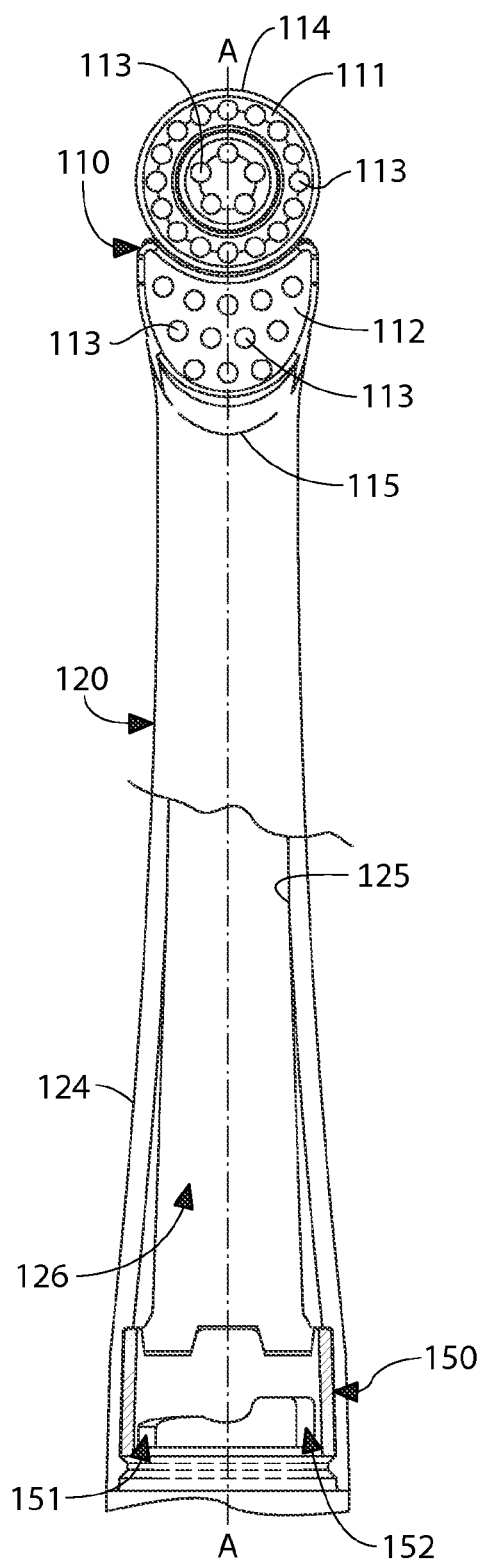
FIG. 2 is a front view of a refill head according to one embodiment of the present invention, wherein the refill head is in partial cut-away.
Figure 3:
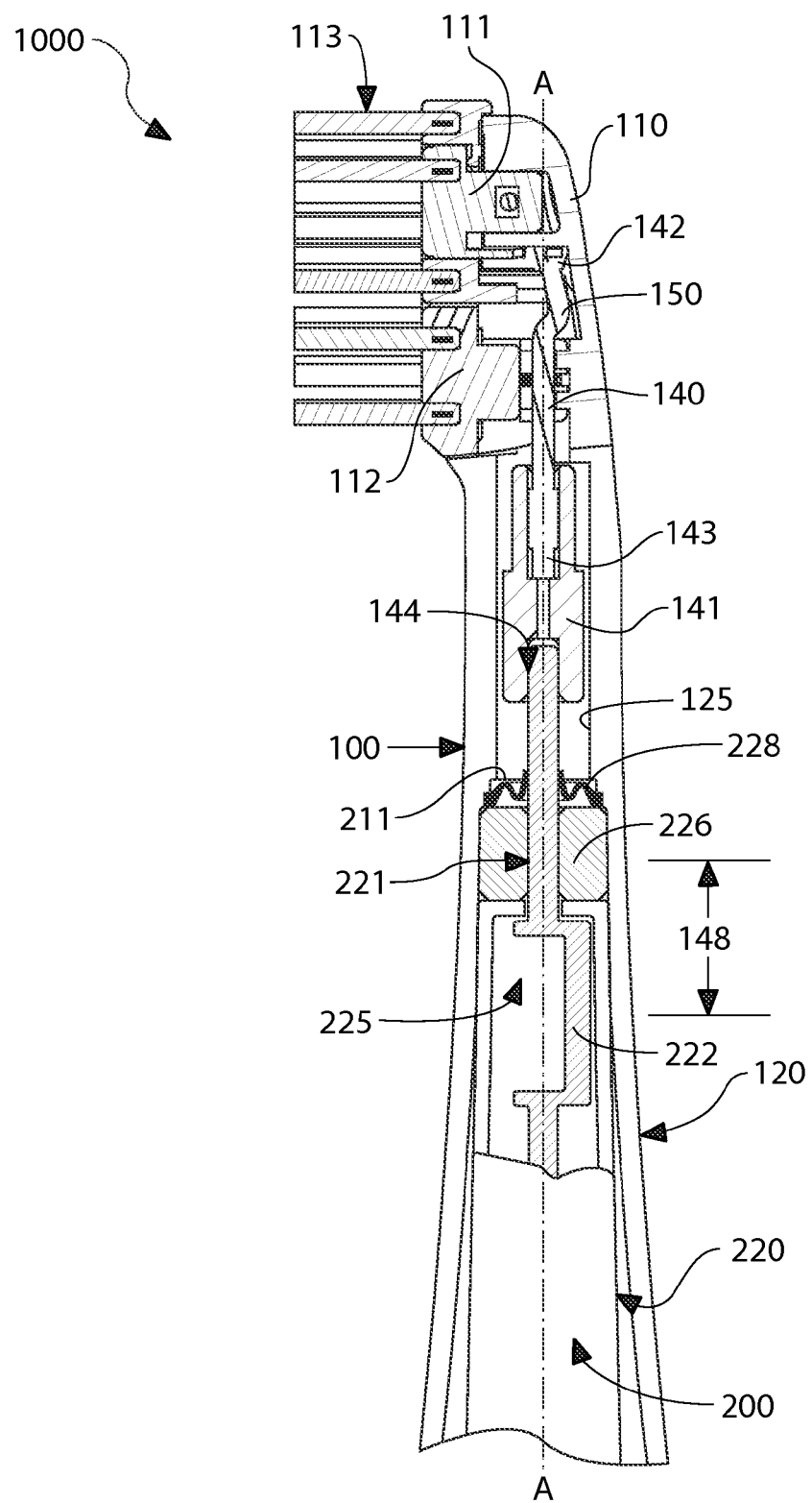
FIG. 3 is a longitudinal cross-sectional schematic of the refill head of FIG. 2.

Referring to FIGS. 1-3 concurrently, a powered toothbrush 1000 according to one embodiment of the present invention is illustrated. The powered toothbrush 1000 generally comprises a refill head 100 and a handle 200. As discussed in greater detail below, the refill head 100 and the handle 200 are designed so that the refill head 100 can be repetitively coupled to and uncoupled from the handle 200. In FIG. 1, the powered toothbrush 1000 is illustrated in a state wherein the refill head 100 is not coupled to the handle 200 but is positioned in axial alignment with the handle 200 so that such coupling can be effectuated. In FIG. 3, the powered toothbrush 1000 is illustrated in a state wherein the refill head 100 is detachably coupled to the handle 200 according to an embodiment of the present invention.

While the invention is exemplified herein as a powered toothbrush 1000, it is to be understood that the inventive concepts discussed herein can be applied to other powered oral care implements, including without limitation tongue cleaners, water picks, interdental devices, tooth polishers and specially designed ansate implements having tooth cleaning elements.

The handle 200 generally comprises a gripping portion (not illustrated) and a stem 220. The stem 220 extends from the gripping portion along a longitudinal axis A-A. The stem 220 further comprises an inner surface 232 and an outer surface 233. The inner surface 232 defines a cavity 225. The stem 220 comprises a proximal portion 261, a middle portion 262 and a distal portion 263.

The gripping portion (not illustrated) of the handle 200 is an elongated structure that provides the mechanism by which the user can hold and manipulate the powered toothbrush 1000 during use. The gripping portion can take on a wide variety of shapes, contours and configurations, none of which are limiting of the present invention. Included within the gripping portion is a power source, an electric motor and the electrical circuitry and components necessary to create the desired motions within the refill head 100. The gripping portion also includes the user interface that controls the various operations of the toothbrush 1000, including without limitation turning off and on, changing speeds of the motor, or other functions. The gripping portion, in essence, forms a watertight housing for the aforementioned electrical circuit and mechanical components that need to be protected from moisture.

In the exemplified embodiment, the refill head 100 is coupled to the handle 200 by a cam-follower assembly. Specifically, the stem 220 comprises a first boss 221 and a second boss 222 that extend radially outward from an outer surface 233 of the stem 220. The first and second bosses 221, 222 are arranged on the stem 220 in a circumferentially spaced apart manner. In the exemplified embodiment, the first and second bosses 221, 222 are approximately 180° apart. Of course, other angular degrees of separation can be utilized as desired. Moreover, in alternate embodiments, more or less than two bosses 221, 222 can be included on the stem 220. The bosses 221, 222 of the stem 220 mate with axial slots 151, 152 of a cam collar 150 that is located within the refill head 100. The cooperation between the bosses 221, 222 and the axial slots 151, 152 facilitates coupling of the refill head 100 to the handle 200. Of course, the invention is not limited to a cam-follower arrangement and in other embodiments the refill head 100 can be detachably coupled to the handle 200 via a snap-fit assembly, a tight-fit assembly, a threaded connection, a male-female-interlock assembly, and combinations thereof. In the exemplified embodiment, the coupling is achieved between a proximal portion 155 of the refill head 100 (and more specifically, in a proximal portion 155 of a cavity 126 of a tubular sleeve 120 of the refill head 100) and a base portion 156 of the stem 220.

The refill head 100 generally comprises a head portion 110 and a tubular sleeve 120 that is coupled to the head portion 110. In the exemplified embodiment, the tubular sleeve 120 and the head portion 110 of the refill head 100 are integrally formed as a single unitary structure using a molding, milling, machining or other suitable process. However, in other embodiments the head portion 110 and the tubular sleeve 120 of the refill head 100 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners.

The tubular sleeve 120 and the head portion 110 of the refill head 100 are generally formed of a material that is rigid, such as a moldable hard plastic. Suitable hard plastics include, without limitation, polymers and copolymers of ethylene, propylene, butadiene, vinyl compounds and polyesters such as polyethylene terephthalate. Of course, the invention is not to be so limited and other materials can be used to form the tubular sleeve 120 and the head portion 110 of the refill head 100 in alternate embodiments.

In the exemplified embodiment, the head portion 110 comprises a movable tuft block 111 and a static tuft block 112. The movable tuft block 111 is positioned adjacent a distal end 114 of the head portion 110 and the static tuft block 112 is positioned adjacent a proximal end 115 of the head portion 110. It should be noted, however, that the invention is not limited to the head portion 110 including only a single movable tuft block 111 and/or only a single static tuft block 112. In certain other embodiments, the head portion 110 may have more than one movable tuft block 111 and/or, more than one static tuft block 112. Furthermore, in other embodiments of the invention, the movable tuft block 111 may be positioned adjacent the proximal end of the head 115 and the static tuft block 112 may be positioned adjacent the distal end 114 of the head. In the exemplified embodiment, the movable tuft block 111 and the static tuft block 112 are axially aligned. However, in other embodiments the movable tuft block 111 and the static tuft block 112 may be transversely aligned or aligned at an angle relative to the longitudinal axis A-A.

Each of the movable and static tuft blocks 111, 112 comprise a plurality of tooth cleaning elements 113 extending outwardly therefrom for cleaning and/or polishing contact with an oral surface and/or interdental spaces. In the exemplified embodiment, the tooth cleaning elements 113 are illustrated in concentric circles on the movable tuft block 111 and in staggered rows on the static tuft block 112. However, the invention is not to be limited the exemplified arrangement of the tooth cleaning elements 113 on either the movable tuft block 111 or static tuft blocks 112.

While the collection of tooth cleaning elements 113 are exemplified as bristles that are particularly suited for brushing teeth, the collection of tooth cleaning elements 113 can also be used to polish teeth instead of or in addition to cleaning teeth. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 113 of the present invention can be connected to the refill head 100 in any manner known in the art. For example, staples/anchors, in-mold tufting (IMT) or anchor free tufting (AFT) could be used to mount the tooth cleaning elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The tubular sleeve 120 of the refill head 100 has an outer surface 124 and an inner surface 125. The inner surface 125 defines a cavity 126. The inner surface 125 of the tubular sleeve 120 also comprises a shoulder 127. When the refill head 100 is coupled to the handle 200, the stem 220 of the handle 200 is disposed within the cavity 126 of the tubular sleeve 120 of the refill head 100. The shoulder 127 can be used to prevent over-insertion of the stem 220 into the cavity 126 when the refill head 100 is coupled to the handle 200. The cavity 126 of the tubular sleeve 120 comprises a distal portion 154, a middle portion 153 and the proximal portion 151.

The handle 200 further comprises components that enable multiple types of motion to be transmitted to the movable and static tuft blocks 111, 112. One of the types of motion that is transmitted to the head portion 110 of the refill head 100 is a vibratory motion. In order to generate such vibratory motion, the handle 200 comprises a vibratory element, which in the exemplified embodiment is in the form of an eccentric 222 coupled to a primary drive shaft 221. The primary drive shaft 221, which is disposed within the stem 220, has a distal portion 223 that protrudes from a distal end 211 of the stem 220. A portion 226 of the distal portion 223 of the primary drive shaft 221 is retained by an annular bearing 224 which is mounted to the stem 220. In the exemplified embodiment, the annular bearing 224 is a hardened steel bearing. Of course, the invention is not so limited and the annular bearing 224 may take on other forms in alternate embodiments. Furthermore, a gasket 228 is located within the stem 220 to surround and seal the distal portion 223 of the primary drive shaft 221. The gasket 228 prevents water, toothpaste and other liquids from entering into the cavity 225 of the stem 220 when the refill head 100 is detached from the handle 200. The primary drive shaft 221 also comprises the eccentric 222 that is disposed within the stem 220. A proximal portion (not illustrated) of the primary drive shaft 221 is operably coupled to the electric motor (not illustrated) so that the electric motor can rotate the primary drive shaft 221.

As the primary drive shaft 221 is rotated, the eccentric 222, due to its off-center center of gravity, generates vibrations that are transmitted to the stem 220 and to the refill head 100 (discussed in greater detail below). While the eccentric 222 is exemplified as a portion of the primary drive shaft 221 that is radially offset from the longitudinal axis A-A, the invention is not so limited. In other embodiments, the eccentric 222 may be an offset disc or other offset weight, as is known in the art. As can be seen in FIG. 1, the stem 220 forms a watertight housing (with the assistance of the gasket 228) having the internal cavity 225 in which the primary drive shaft 221 and eccentric 222 are housed. Additional details of a suitable vibratory producing handle, and related structure, that can be incorporated into the powered toothbrush 1000 of the present invention can be found in U.S. Patent Application Publication No. 2010/0269275, Shimoyama et al., published Oct. 28, 2010 (filed as U.S. patent application Ser. No. 12/377,355), the entirety of which is hereby incorporated by reference.

The tubular sleeve 120 comprises a vibration transmission portion 148 which is an axial portion of the tubular sleeve 120 that is in intimate surface contact with the outer surface 233 of the stem 220 when the refill head 100 is coupled to the handle 200. In the exemplified embodiment, only the outer surface 233 of the distal portion 263 of the stem 220 is in intimate surface contact with the inner surface 125 of the tubular sleeve 120. The vibration transmission portion 148 of the tubular sleeve 120 is located at or within the middle portion 153 of the cavity 126 of the refill head 200. Thus, when the refill head 100 is operably coupled to the handle 200, the eccentric 222 is located in the middle portion 153 of the cavity 126 to generate vibrations and transmit the vibrations to the head portion 110. This structural arrangement permits vibrations from the stem 220 to be transmitted directly to the refill head 100 while minimizing the amount of vibrations that is transmitted to the handle 200. Minimizing vibrations to the handle 200 enhances the comfort of the powered toothbrush 1000 during use.

In addition to the vibrations that are imparted to the refill head 100, the handle 200 of the powered toothbrush 1000 also imparts rotational movement to the movable tuft block 111. In order to facilitate rotational movement to the movable tuft block 111, the distal portion 223 of the primary drive shaft 221 is operably coupled to the movable tuft block 111. In the exemplified embodiment, the primary drive shaft 221 is indirectly coupled to the movable tuft block 111 as described below. However, in certain other embodiments the primary drive shaft 221 can be directly coupled to the movable tuft block 111.

In the exemplified embodiment, the refill head 100 comprises a secondary drive shaft 140 and a drive shaft adapter 141. The drive shaft adapter 141 is located in the distal portion 154 of the tubular sleeve 120. More specifically, the drive shaft adapter 141 is located in the distal portion of the cavity 126 of the tubular sleeve 120. The drive shaft adapter 141 comprises an axial cavity 144 for receiving at least a portion of the distal portion 223 of the primary drive shaft 221 therein when the refill head 100 is coupled to the handle 200. The axial cavity 144 receives the portion of the primary drive shaft 221 that protrudes from the distal end 211 of the stem 220. The secondary drive shaft 140 comprises a first end 142 that is operably coupled to the movable tuft block 111 and a second end 143 that is operably coupled to the drive shaft adapter 141. The first end 142 of the secondary drive shaft 140 comprises an offset portion 150. The offset portion 150 of the first end 142 of the secondary drive shaft 140 is a portion that is offset from the longitudinal axis A-A. The offset portion 150 enables the secondary drive shaft 140 to rotate (which can be full rotation or limited oscillation) the movable tuft block 111 in a desired fashion as described below.

Thus, by virtue of the secondary drive shaft 140, rotation is imparted to the movable tuft block 111. In other words, the motor drives the primary drive shaft 221, which in turn drives the secondary drive shaft 140 via coupling of both the primary drive shaft 221 and the secondary drive shaft 140 to the drive shaft adapter 141. Thus, the secondary drive shaft 140 rotates via operable (yet indirect) coupling to the motor, which in turn rotates the movable tuft block 111. In this manner, rotation of the primary drive shaft 221 by the motor results in both the eccentric 222 generating vibrations within the stem 220 that are transmitted to the head portion 110 and rotational movement of the movable tuft block 111. In some embodiments, the vibrations from the eccentric 222 only create vibrations that vibrate the tooth cleaning elements 113 of the static tuft block 112. However, in other embodiments the vibrations vibrate the tooth cleaning elements 113 of both the movable and static tuft blocks 111, 112.

Thus, the present invention allows for a refill head 100 that has a movable tuft block 111 that is capable of rotating when the refill head 100 is operably coupled to the handle 200 and wherein vibrations are separately generated and transmitted to the head portion 110 of the refill head 100. As described above, in certain embodiments the secondary drive shaft 140 may be omitted and the primary drive shaft 221 will protrude further from the distal end 211 of the stem 220 so that when the refill head 100 is operably coupled to the handle 200, the distal end of the primary drive shaft 221 will be directly coupled to the movable tuft block 111. However, with the exemplified embodiment the drive shaft adapter 141 enables the movement imparted to the primary drive shaft 221 via the motor to be further imparted onto the secondary drive shaft 140 for causing the movable tuft block 111 to rotate.

Rotation of the movable tuft block 111 can be any type of rotation known in the art. More specifically, the movable tuft block 111 may rotate in a circular fashion in one of the clockwise or counter clockwise directions. Alternatively, the movable tuft block 111 may oscillate in a repeated back-and-forth manner. Further still, in other embodiments, the movable tuft block 111 may move up-and-down in the axial direction or side-to-side in a transverse direction. Thus, the exact type of motion imparted to the movable tuft block 111 via the primary drive shaft 221 (and secondary drive shaft 140 as necessary) is not limiting of the present invention.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. A powered toothbrush comprising:
   a handle comprising:
      a gripping portion; and
      a stem extending from the gripping portion, the stem extending along an axis; and
      a power source, an electric motor and a primary drive shaft operably coupled together, the primary drive shaft comprising a distal portion protruding from a distal end of the stem and an eccentric disposed within stem;
   a refill head detachably coupled to the handle, the refill head comprising:
      a head portion comprising at least one movable tuft block comprising a plurality of tooth cleaning elements;
      a tubular sleeve coupled to the head portion, the tubular sleeve having a cavity in which the stem is disposed; and
      the distal portion of the primary drive shaft operably coupled to the movable tuft block; and
   wherein rotation of the primary drive shaft by the motor results in: (1) the eccentric of the primary drive shaft generating vibrations within the stem that are transmitted to the head portion; and (2) rotational movement of the movable tuft block.

2. The powered toothbrush according to claim 1 wherein the head portion further comprises at least one static tuft block comprising a plurality of tooth cleaning elements, the vibrations vibrating the plurality of tooth cleaning elements of the static tuft block.

3. The powered toothbrush according to claim 2 wherein the movable tuft block and the static tuft block are axially aligned, and wherein the static tuft block is adjacent a proximal end of the head portion.

4. The powered toothbrush according to claim 1 wherein the refill head further comprises a secondary drive shaft and a drive shaft adapter, the secondary drive shaft having a first end operably coupled to the movable tuft block and a second end operably coupled to the drive shaft adapter, and wherein the distal portion of the primary shaft is operably coupled the drive shaft adapter.

5. The powered toothbrush according to claim 4 wherein the drive shaft adapter comprises an axial cavity for slidably receiving the distal portion of the primary shaft.

6. The powered toothbrush according to claim 4 wherein the first end of the secondary drive shaft comprises an offset portion.

7. The powered toothbrush according to claim 4 wherein the drive shaft adapter is located in a distal portion of the cavity and the tubular sleeve comprises a vibration transmission portion configured to be in intimate surface contact with an outer surface of the stem, the vibration transmission portion located at a middle portion of the cavity.

8. The powered toothbrush according to claim 1 wherein the handle further comprises an annular bearing coupled to the stem that retains the distal portion of the primary drive shaft.

9. The powered toothbrush according to claim 1 wherein an inner surface of the tubular sleeve comprises a shoulder that prevents over-insertion of the stem into the cavity.

10. The powered toothbrush according to claim 1 further comprising a gasket surrounding and sealing around the distal portion of the primary drive shaft.

11. The powered toothbrush according to claim 1 wherein the refill head is detachably coupled to the handle via a coupling selected from a group consisting of a snap-fit assembly, a cam-follower assembly, a tight-fit assembly, a threaded connection, a male-female-interlock assembly, and combinations thereof.

12. The powered toothbrush according to claim 11 wherein the coupling is located in a proximal portion of the tubular sleeve and a base portion of the stem.

13. The powered toothbrush according to claim 12 wherein the eccentric is located in a distal portion of the stem.

14. The powered toothbrush according to claim 13 wherein only an outer surface of the distal portion of the stem is in intimate surface contact with an inner surface of the tubular sleeve.

* * * * *